United States Patent [19]

Nishino et al.

[11] Patent Number: 4,755,473

[45] Date of Patent: Jul. 5, 1988

[54] METHOD OF DETECTING CARBON DIOXIDE GAS

[75] Inventors: Tadashi Nishino, Tokyo; Masayuki Nagai, Kanagawa, both of Japan

[73] Assignee: Sekisui Kaseihin Kogyo Kabushiki Kaisha, Nara, Japan

[21] Appl. No.: 863,891

[22] Filed: May 16, 1986

[30] Foreign Application Priority Data

May 16, 1985 [JP] Japan ................................ 60-102666
Apr. 15, 1986 [JP] Japan ................................. 61-85126

[51] Int. Cl.$^4$ ............................................ G01N 27/12
[52] U.S. Cl. .................................... 436/133; 436/151; 422/98; 73/23; 73/336.5
[58] Field of Search .................... 422/98, 90; 436/133, 436/151; 73/336.5, 23 R; 338/34

[56] References Cited

U.S. PATENT DOCUMENTS 4,419,889 12/1983 Muto et al. .......................... 73/336.5

FOREIGN PATENT DOCUMENTS 0026401 3/1981 Japan ...................................... 338/34

OTHER PUBLICATIONS

Nagai et al., Complex Impedance Behavior of Porous Hydroxyapatite Ceramics, *Ceramics Association Annual Meeting, Preliminary Publication*, 411 (1985).

Primary Examiner—Michael S. Marcus
Assistant Examiner—Jill Johnston
Attorney, Agent, or Firm—Armstrong, Nikaido, Marmelstein & Kubovcik

[57] ABSTRACT

The presence of carbon dioxide contained in a gas can be detected through measurement of the change in the electrical resistance of a hydroxyapatite in contact with carbon dioxide gas. The sensitivity of the hydroxyapatite to carbon dioxide gas can be enhanced by the formation of a composite of the hydroxyapatite with an inorganic carbonate, e.g., sodium carbonate or calcium carbonate. The sensitivity to carbon dioxide gas can be further enhanced by the formation of a composite of the hydroxyapatite with an inorganic halide, e.g., calcium chloride.

4 Claims, 7 Drawing Sheets

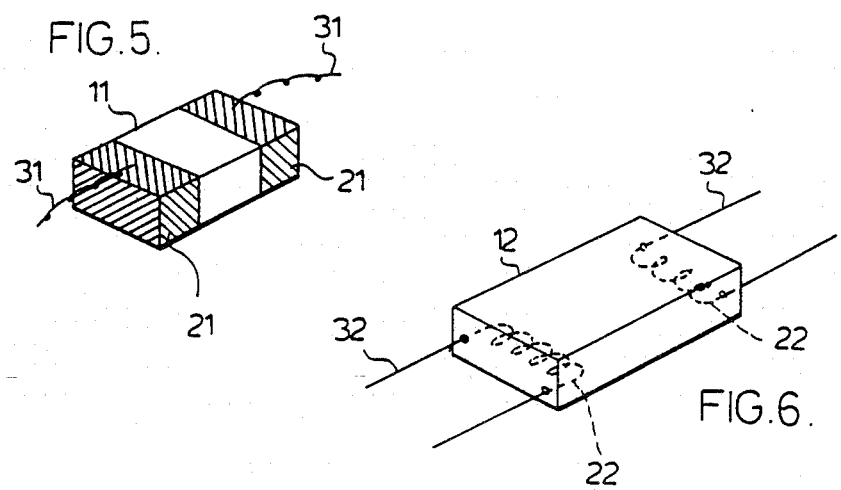
FIG. 5.
FIG. 6.
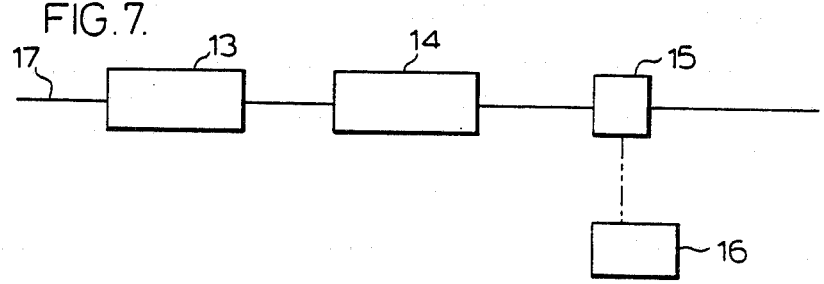
FIG. 7.
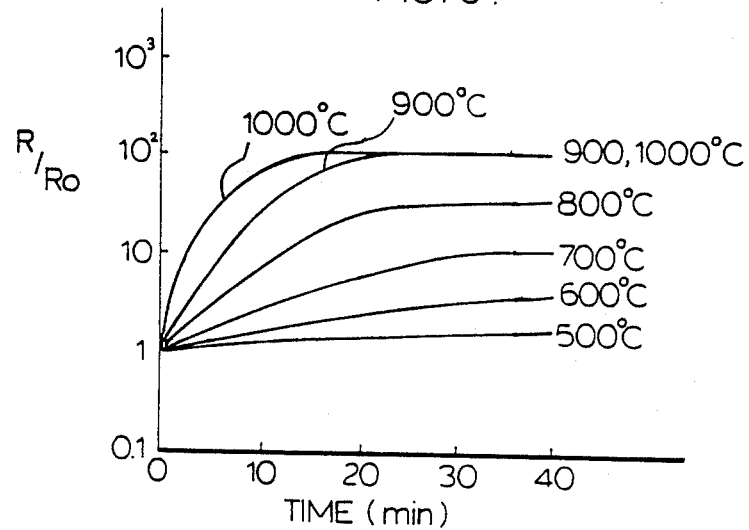
FIG. 8.

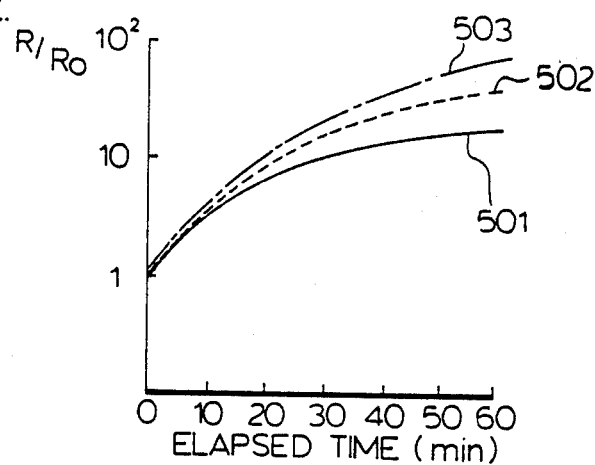
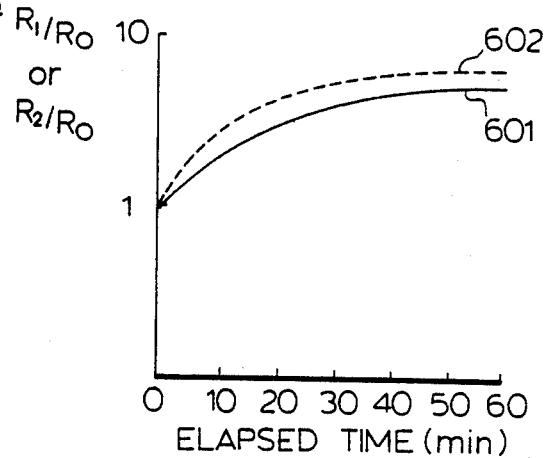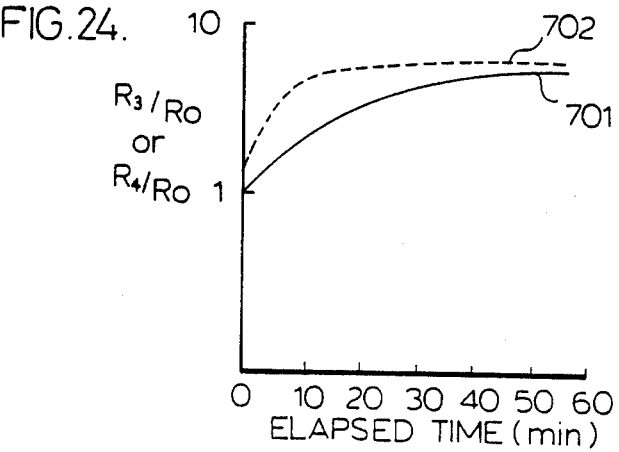

METHOD OF DETECTING CARBON DIOXIDE GAS

FIELD OF THE INVENTION

The present invention relates to a method for detecting carbon dioxide gas, an element for detecting the gas, and a process for producing the same.

The present invention can be utilized in various fields, such as, for example, for the control of the concentration of carbon dioxide gas in a hothouse for agricultural cultivation (agricultural use), for the monitoring of exhaust gases (industrial use), for the control of living environments (use for environmental sanitation), for the early detection of fires (use for the prevention of disasters), and the like.

BACKGROUND OF THE INVENTION

Various sensors capable of detecting the presence of a specific component (e.g., hydrocarbons, oxygen or carbon monoxide) contained in a gas have been developed for such purposes as the prevention of disasters, effective operation of machines or plants, and the like. However, unlike such gases as hydrocarbons, oxygen and carbon monoxide, carbon dioxide is chemically stable and, therefore, it is difficult to detect with sufficient sensitivity with a gas sensor utilizing hitherto known principles, e.g., an adsorption reaction or a combustion reaction of such a gas (see, e.g., U.S. Pat. No. 4,343,768).

It is known that carbon dioxide gas generates, when dissolved into water, hydrogen ions in proportion to the quantity dissolved therein and, hence, the concentration of carbon dioxide gas can be measured indirectly by measuring the concentration of hydrogen ion by use of a pH meter and a glass electrode (see U.S. Pat. No. 4,376,681). This method, however, requires a long period of time to dissolve carbon dioxide contained in a sample gas into water and remove it therefrom. In addition, the measurement tends to be strongly influenced by the presence of such foreign gases as $SO_x$, $NO_x$ and $NH_3$, which also could change the pH of the aqueous solution to be measured.

There is also known a method for detecting carbon dioxide gas, in which a sample of gas or fluid containing carbon dioxide gas, bicarbonate ion and/or carbonate ion is allowed to come into contact with an acid extracting fluid; a carbon dioxide-free gas is passed through the fluid in order to carry the dissolved carbon dioxide gas onto a carbon dioxide absorbing tube provided with an alkaline solution with a resulting change in the electrical conductivity of the alkaline solution, thus making it possible to measure the concentration of carbon dioxide gas contained in the sample (see U.S. Pat. No. 4,321,545). However, this method, like the above method using a pH meter, not only requires a long period of time for dissolving and removing carbon dioxide gas, but also is unable to distinguish the kind of ions detected. In addition, an apparatus to be used for the measurement could hardly be small in size.

There is also known a method utilizing the characteristic absorption of carbon dioxide gas in the infrared region of the spectrum. In general, a sensor utilizing this method consists of an IR ray generation section from which an IR beam with a wavelength of 4.25 μm is emitted, a cell having a path length of several meters, an IR detector, and a fan which draws air through the cell. An apparatus utilizing the method, therefore, is expensive and could hardly be small in size. In addition, measurements utilizing the method are susceptible to the influence of dusts and other contaminants.

It is, therefore, desired, to develop a small and light carbon dioxide gas sensor capable of detecting the gas with a high accuracy and a quick response, without being influenced by dusts or the like.

In view of the above objective, the present inventors have conducted intensive investigations and found that carbon dioxide gas can be detected by utilizing a hydroxyapatite, which so far is known to be a porous ceramic usable as a moisture sensor since its electrical resistance changes in response to the change in moisture (see Japanese Patent Application (OPI) No. 166,249/83). (The term "OPI" as used herein refers to a "published unexamined Japanese patent application".) The moisture sensor of a hydroxyapatite utilizes the physical phenomenon that water absorbed on the surface of a hydroxyapatite penetrates into the pores of the porous ceramic and condenses therein. On the other hand, it has now been found that when a hydroxyapatite is brought into contact with carbon dioxide gas, carbonate apatite is formed therefrom in proportion to the concentration of carbon dioxide gas and, hence, the carbon dioxide gas can be detected through measurement of the change in its electrical resistance because the thus formed carbonate apatite has a greater electrical resistance than the hydroxyapatite. The present invention has been accomplished based on the above finding.

SUMMARY OF THE INVENTION

According to the present invention, the presence of carbon dioxide contained in a gas can be detected by bringing a hydroxyapatite represented by formula (I):

$$M_{10}(ZO_4)_6(OH)_2 \qquad (I)$$

wherein M is an element selected from the group consisting of Ca, Ba, St, Pb and Cd; and Z is an element selected from the group consisting of P, As and V, into contact with a gas containing carbon dioxide, and measuring the change in the electrical resistance of the hydroxyapatite caused by the contact with the carbon dioxide gas.

The detection of the presence of carbon dioxide gas can be effected with an increased sensitivity by bringing a carbon dioxide gas detection element comprising a composite of a hydroxyapatite represented by the above formula (I) and an inorganic carbonate into contact with a gas containing carbon dioxide in order to attain an increased change in its electrical resistance upon contact with carbon dioxide.

The detection of the presence of carbon dioxide gas can be effected with a much increased sensitivity even at a low temperature by using a carbon dioxide gas detection element which comprises a composite of a hydroxyapatite represented by the above formula (I) and an inorganic halide and bringing it into contact with carbon dioxide in order to enhance the change in its electrical resistance.

It is an object of the present invention to provide a method for detecting the presence of carbon dioxide contained in a gas.

It is another object of the present invention to provide a carbon dioxide gas detection element capable of detecting the presence of carbon dioxide gas contained in a gas with a high sensitivity.

It is a further object of the present invention to provide a carbon dioxide gas detection element which makes it possible to detect the presence of carbon dioxide gas contained in a gas by a simple means.

BRIEF DESCRIPTION OF THE DRAWING

FIG. 5 is a perspective view showing a carbon dioxide gas detection element of a porous type according to the invention;

FIG. 6 is a perspective view showing a carbon dioxide gas detection element according to the invention provided with a wire lead which also functions as a heater;

FIG. 7 is a flow chart showing an example of practicing the process for detecting carbon dioxide gas according to the invention;

FIG. 8 is a graph showing the change in the electrical resistance, due to the change in its temperature, of a hydroxyapatite contacted with carbon dioxide;

FIG. 22 is a graph showing the results of the test in Example 12;

FIG. 23 is a graph showing the results of the test in Example 13; and

FIG. 24 is a graph showing the results of the test in Example 14.

DESCRIPTION OF THE PREFERRED EMBODIMENT

Figure 1:
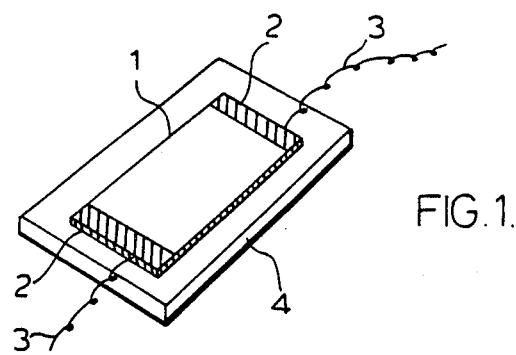
FIG. 1 is a perspective view showing a carbon dioxide gas detection element according to the invention in which a thin layer of a hydroxyapatite or composites thereof is utilized.
Figure 2:
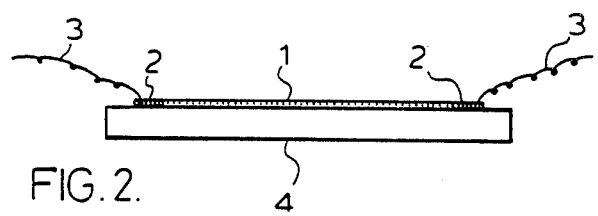
FIG. 2 is a side view of the element shown in FIG. 1.

The hydroxyapatite represented by formula (I);

$$M_{10}(ZO_4)_6(OH)_2 \tag{I}$$

wherein M is an element selected from the group consisting of Ca, Ba, Sr, Pb and Cd; and Z is an element selected from the group consisting of P, As and V, may be prepared by known methods, including, e.g., wet, dry and hydrothermal processes. Any hydroxyapatite having formula (I) can be used in the present invention. However, it is preferable to use a hydroxyapatite represented by formula (I) wherein M is Ca and Z is P.

Further, compounds of formula (I) may also contain small amounts of the elements Sc, Y, Tl, Bi, V, Ni, Mn, Fe, Sn, Rb, Na, K, and Cs in addition to those elements listed for element M and small amounts of the elements Si, Ge, Cr, Mn, Al, and B in addition those elements listed for element Z.

A porous sintered material of a hydroxyapatite can be obtained by molding powders of a hydroxyapatite in a mold of, such as a pellet molding machine with the application of pressure and then sintering the molded product in an electric furnace at a temperature of from 800° to 1,000° C., preferably from 850° to 950° C., for a period of 1 hour or more, preferably from 1.5 to 2.5 hours.

In the case where a thin layer sintered material is to be obtained, the hydroxyapatite may be mixed with water and an organic binder, e.g., a methyl cellulose, to form a slurry, which can be coated on a refractory substrate or base in the form of a thin layer. The coated product may then be sintered at a temperature of from 800° to 1,000° C., preferably from 800° to 950° C., for a period of 1 hour or more, preferably from 1.5 to 2.5 hours.

The thus prepared porous sintered product can be immersed in an aqueous inorganic carbonate solution and then dried to allow the inorganic carbonate to attach on the surface of the hydroxyapatite, thereby forming a composite of a hydroxyapatite and an inorganic carbonate according to the invention.

Any inorganic carbonate which increases the variation in electrical resistance due to the contact of the hydroxyapatite with carbon dioxide gas can be used in the present invention. It is preferred to use a sodium carbonate or calcium carbonate.

Similarly, a hydroxyapatite-inorganic halide composite material of a carbon dioxide gas detection element according to the invention can be produced by immersing a porous sintered product of a hydroxyapatite in an aqueous inorganic halide solution and drying it to thereby deposit the inorganic halide on a surface of the hydroxyapatite.

In the present invention, there can be used any inorganic halide which is capable of enhancing the change in the electrical resistance of the hydroxyapatite upon contact with gaseous carbon dioxide. It is, however, preferable to use calcium chloride, ammonium chloride or mixtures thereof.

A carbon dioxide gas detection element can be produced by providing electrodes and wire leads at the both ends of the material comprising the hydroxyapatite, the hydroxyapatite-inorganic carbonate composite, or the hydroxyapatite-inorganic halide composite according to the invention.

A carbon dioxide gas detection element according to the invention can also be produced by providing electrodes and wire leads at both ends of a porous sintered product of a hydraxyapatite and then immersing it in an aqueous inorganic carbonate solution, followed by drying it to form a composite of the hydroxyapatite and the inorganic carbonate.

Similarly, a hydroxyapatite-inorganic halide composite material of a carbon dioxide gas detection element according to the invention can be produced by immersing a porous, sintered product of a hydroxyapatite, which is provided with electrodes and wire leads, in an aqueous inorganic halide solution and drying it to thereby deposit the inorganic halide on a surface of the hydroxyapatite.

The immersion of the sintered hydroxyapatite into the aqueous solution of an inorganic carbonate or of an inorganic halide may be carried out in two stages: firstly under a reduced pressure, e.g., 1/10 of atmospheric pressure in the first stage, and then at atmospheric pressure in the second stage. When the immersion is carried out in two stages as above, the inorganic carbonate or the inorganic halide contained in the aqueous solution of the carbonate or the halide can be distributed throughout the pores of the sintered product to form a hydroxyapatite-inorganic carbonate composite or a hydroxyapatite-inorganic halide composite on the entire surface of the hydroxyapatite.

The amount of the composites formed by the immersion can be increased by using in the immersing treatment an aqueous inorganic carbonate or halide solution containing the carbonate or halide in an increased amount. The electrical resistance of the detection element decreases with the increase in the amount of the composite contained therein. This makes the increase in the electrical resistance of the composites observed upon contact with gaseous carbon dioxide greater, i.e., makes the element more sensitive to gaseous carbon dioxide. Accordingly, the presence of carbon dioxide contained in a gas can be detected by the use of the detection element according to the invention even at a relatively low temperature, e.g., at around room temperature.

In the hydroxyapatite, the electrical resistance is increased by the presence of carbon dioxide in a gas, but it is slightly decreased when moisture is present in the gas. Accordingly, in order to completely remove the influence by the moisture in the gas, it is required to remove the moisture in the gas in advance, or the detection may be carried out at an elevated temperature, e.g., as high as 500° C. or above, so as to make the sensitivity of the element higher and, at the same time, to make the relative humidity of the gas low enough not to disturb the detection of gaseous carbon dioxide.

However, since the detection element comprising the hydroxyapatite-carbonate or hydroxyapatite-halide composite according to the invention has a sufficiently high sensitivity to carbon dioxide gas, it can detect the carbon dioxide gas in the presence of moisture at a relatively low temperature, e.g., at a temperature around room temperature, or at a temperature around 300° C.

As described above, a carbon dioxide gas detection element can be prepared by providing electrodes and wire leads at the both ends of the hydroxyapatite or composites thereof, or by forming a thin layer of the hydroxyapatite or composites thereof on an insulating base, followed by bonding electrodes and wire leads to both ends of the thin layer. The thin layer formed on an insulating base can be mounted on or above a heater positioned on a refractory substrate or base to give a detection element that can be used at elevated temperatures.

A pair of plates of electrodes can be provided on an alumina substrate or base, and then a platinum paste can be coated and dried thereon. On the electrodes of the alumina substrate or base can be placed the thin layer of the hydroxyapatite prepared as above, and then sintered at a temperature not lower than 500° C., preferably from 700° C. to 1,000° C., to give a detection element for carbon dioxide gas with platinum as a noble metal positioned between the hydroxyapatite and the electrodes.

The thus prepared detection element material can then be immersed in an aqueous solution of an inorganic carbonate or halide, in order to impregnate the halide into the porous hydroxyapatite. Thereafter, it can be taken out of the solution and dried to give a detection element comprising composites of the carbonate apatite and the noble metal, or of the halide apatite and the noble metal. The resulting material can then be heated at a constant temperature in the range of from 100° C. to 600° C., preferably at 400° C., for at least 30 minutes, preferably from 1 to 3 hours, and cooled to give a highly sensitive detection element material according to the invention.

In a carbon dioxide gas detection element according to the present invention, a noble metal such as platinum, palladium, rhodium, gold, or silver or a salt thereof and an inorganic carbonate or an inorganic halide can jointly form a composite with a hydroxyapatite. Any noble metal or salt thereof, or a mixture thereof which makes the variation in electrical resistance due to the contact of the hydroxyapatite with carbon dioxide gas great can be used in the present invention. It is, however, preferable to use platinum, palladium chloride or mixtures thereof. Since palladium chloride is soluble in water, a composite between the hydroxyapatite and palladium chloride as a noble metal can be formed by immersing the former in an aqueous solution of the latter, as in the case of the inorganic carbonate or the halide.

In the preparation of the detection element for carbon dioxide gas according to the invention, the element comprising the composite with an inorganic halide can be brought, during the heating at a constant temperature in the range of from 100° C. to 600° C. (e.g., at a working temperature of 400° C.), into contact with a conditioning gas which contains carbon dioxide gas, so as to further enhance its sensitivity to gaseous carbon dioxide. The concentration of carbon dioxide in the conditioning gas can be lower than in a simple gas to be actually examined. It can be preferable to use a conditioning gas which contains carbon dioxide gas in a concentration as close as possible to that in a sample gas to be actually examined.

The contact between the composite apatites and a sample gas or a conditioning gas can be effected as a pretreatment just before the use of a carbon dioxide detection element prepared from the material according to the invention.

Figure 3:
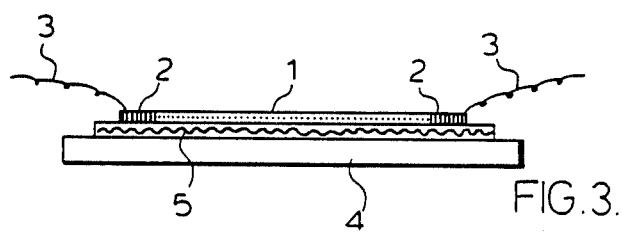
FIG. 3 is a side view showing a carbon dioxide gas detection element according to the invention provided with a heater.

In FIGS. 1, 2, 3 and 4, 1 is a thin layer of the hydroxyapatite or the composites thereof; 2 are electrodes provided at the both ends of the thin layer 1 for measuring its electrical resistance (impedance); 3 are wire leads to connect the electrodes 2 to an apparatus 16 (not shown in FIGS. 1, 2, 3 and 4) for measuring electrical resistance (impedance); and 4 and 41 are a refractory substrate or base to support the thin layer 1. In FIG. 3, 5 is a heater provided on the refractory substrate or base 4 and having provided thereon the thin layer 1.

In FIGS. 5 and 6, 11 and 12 are a porous hydroxyapatite or composites thereof; 21 and 22 are electrodes; and 31 and 32 are wire leads. In the element shown in FIG. 6, either or both of the electrodes 22 and 22 function as a heater and, at the same time, as an electrode.

When the hydroxyapatite is brought into contact with carbon dioxide at a temperature of from 500° to 1,000° C., it changes to a carbonate apatite with a significant change in its electrical resistance, which can be utilized for the detection of the presence of carbon dioxide. Further, in the case of the above-described composite material of the hydroxyapatite, the sensitivity for detecting the carbon dioxide gas can be increased by an increase in temperature at which it is brought into contact with the gas. Accordingly, since the thin layer 1 is used by heating or in a heating atmosphere, it is installed on the refractory substrate or base 4. It is preferred that the thin layer 1 has a thickness not greater than 300 μm (most preferably not greater than 200 μm) and is in a porous state. In cases where the element according to the invention is in the porous form, the wire leads may function as a support, as well. In this case, it is necessary that the wire leads have a sufficient strength and durability.

The element according to the invention is used at an elevated temperature and, hence, the wire leads, as well as the substrate or base, to be used therein are preferably made of a material which can withstand a high temperature at which the detection is to be effected.

FIG. 7 shows an example of a preferable flow chart illustrating the case where a gas to be examined is heated. In the flow sheet; 13 is a dehumidifier; 14 is a heater for a gas to be examined; 15 is a sensor for detecting the presence of carbon dioxide in which a detection element, which may be any of the types shown by FIGS. 1, 3, 4, 5 and 6, is housed; 16 is an apparatus for measuring electrical resistance (impedance) which is connected to the wire leads 3, 31, and 32; and 17 is a line through which the gas flows.

In the flow sheet shown in FIG. 7, the gas to be analyzed is passed through the line 17 and is allowed to enter into the dehumidifier 13, in which the moisture contained in the gas is removed. Thereafter, it is introduced into the heater 14 and then into the sensor 15 for the detection of the presence of carbon dioxide. If carbon dioxide is present in the gas, the measuring apparatus 16 will record a significant increase in the electrical resistance of the detection element, indicating the presence of carbon dioxide. In the case where the gas is heated to a sufficiently high temperature by the heater 14, the relative humidity of the gas could be reduced to an extremely low level even when a substantial amount of moisture is contained therein. In such a case, the influence of the moisture can be limited to a virtually negligible level and, therefore, the dehumidifier 13 may not be required.

FIG. 3 shows an example of a carbon dioxide detection element provided with the thin layer 1 which is to be heated upon measurement. In the element, the heater 5 is provided in the refractory substrate or base 4, and the thin layer 1 provided with the electrodes 2 at the both ends thereof is formed on the heater 5. The thin layer 1 is heated by the heater 5 and is brought into contact with a gas to be examined. If the gas contains carbon dioxide, the electrical resistance of the thin layer 1 increases significantly to indicate the presence of carbon dioxide in the gas examined.

Figure 4:
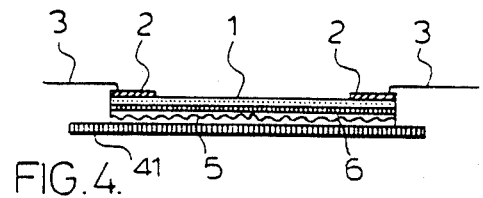
FIG. 4 is a side view showing another carbon dioxide gas detection element according to the invention provided with a heater.

FIG. 4 shows an example in which a heat-resistant electrical insulator 6 is provided between the thin layer 1 and the heater 5 which is provided on the heat-resistant substrate or base 41. In the case where an element of this type or an element of the type shown in FIG. 6, which is provided with a built-in heater, is used, the heater 14 shown in FIG. 7 need not be used.

The electrical resistance increases with the increase in the concentration of carbon dioxide contained in the gas, irrespective of the type of the element used therefor. It is therefore possible to measure the concentration of the carbon dioxide.

Figure 10:
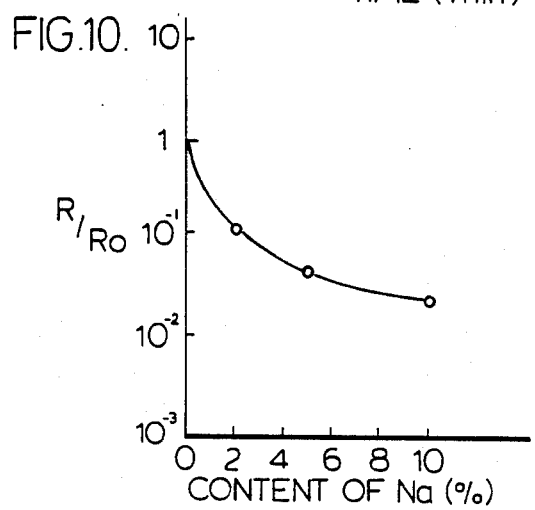
FIG. 10 is a graph showing the relationship between the content of Na in a sodium hydroxyapatite and its electrical resistance.

The increase in the electrical resistance of the element will be small (as shown in FIG. 10) in the case where the hydroxyapatite used therefor is represented by the following formula (I):

$$M_{10}(ZO_4)_6(OH)_2 \qquad (I)$$

wherein M is an element selected from the group consisting of Ca, Ba, Sr, Pb and Cd; and Z is an element selected from the group consisting of P, As and V, and is incorporated with a compound (a minor component) represented by the formula (I), wherein M is an element selected from the group consisting of Sc, Y, Tl, Bi, V, Ni, Mn, Fe, Sn, Rb, Na, K and Cs; and Z is an element selected from the group consisting of Si, Ge, Cr, Mn, Al and B. In such a case, a simpler electrical circuit can be applied to the detection element, irrespective of the type of the element used.

The present invention will further be explained by means of the following, non-limiting Examples.

EXAMPLE 1

Preparation of hydroxyapatite

To 79 g of $(NH_4)_2HPO_4$ was added 1,000 ml of distilled water, and the phosphate was completely dissolved. To this solution was added 5% ammonia water to adjust the pH to 12. As a result, 1,600 ml of an aqueous ammonium phosphate solution was obtained.

Separately, to 236 g of $Ca(NO_3)_2.4H_2O$ was added 1,000 ml of distilled water, and the nitrate was completely dissolved. To this solution was added 5% ammonia water to adjust the pH to 12. As a result, 1,200 ml of an aqueous ammonium calcium nitrate solution was obtained. To the resulting solution was added with stirring the aqueous ammonium phosphate solution prepared above, whereby a white precipitate was formed. The precipitate was filtered off, washed and dried at 250° C. White powders of 100 g of hydroxyapatite were obtained.

EXAMPLE 2

Preparation of porous sintered material of hydroxyapatite

To 50 g of the hydroxyapatite powders prepared in Example 1 was added 20 ml of an aqueous 5% methyl cellulose solution. The resulting mixture was well kneaded to form a slurry of the hydroxyapatite powder. This slurry was coated on a glass plate (200×200×5 mm) at a coverage of 0.05 g/cm$^2$, air dried for 24 hours and then peeled off. Thereafter, it was cut into a size of 15 mm×10 mm, placed on an alumina plate (25×25×0.5 mm), and sintered in an electric furnace at a temperature of 1,000° C. for one hour. The thus prepared hydroxyapatite material had a thickness of 300 μm.

EXAMPLE 3

Change in electrical resistance of hydroxyapatite due to the change in its temperature A carbon dioxide detection element was prepared by providing electrodes at the both ends of the thin layer of the porous sintered hydroxyapatite prepared in Example 2.

The electrical resistance (Ro) of the element was measured in the air. Thereafter, the element was placed in an electric furnace, the air in the furnace was replaced with carbon dioxide gas, and the temperature in the furnace was raised to 500° C., whereby the change in its electrical resistance (R) with a lapse of time was measured, and the ratio R/Ro was recorded.

The above measurement was repeated in the same manner as above, except that the temperature in the furnace was changed to 600°, 700°, 800°, 900°, or 1,000° C.

Results obtained are shown in FIG. 8.

EXAMPLE 4

Change in electrical resistance of hydroxyapatite due to the change in its thickness Carbon dioxide detection elements were prepared in the same manner as in Example 3, except that the thickness of the thin layer of the sintered hydroxyapatite formed on the alumina plate was adjusted to 100, 300, or 500 μm.

The electrical resistances Ro and R of each element were measured in the same manner as in Example 3, except that the temperature in the electric furnace was maintained at 800° C.

Figure 9:
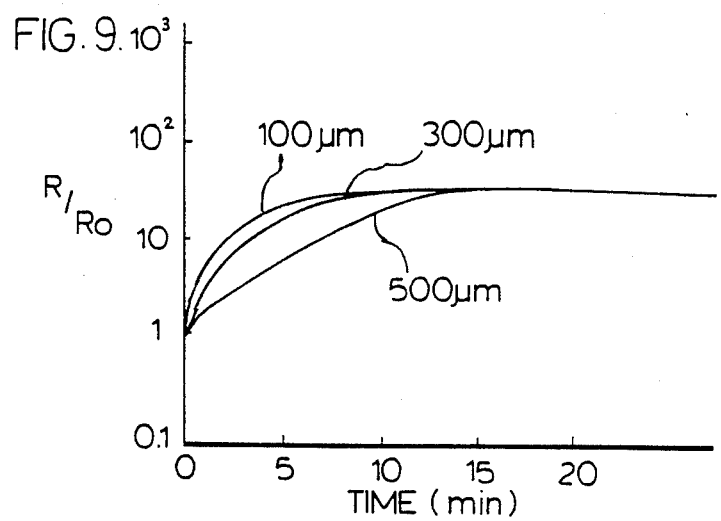
FIG. 9 is a graph showing the change in the electrical resistance, due to the change in its thickness, of a hydroxyapatite contacted with carbon dioxide gas.

Results obtained are shown in FIG. 9.

EXAMPLE 5

Preparation of sodium hydroxyapatite

Powders of sodium hydroxyapatite were prepared In the same manner as in Example 1, except that Na$_2$HPO$_4$ was used in combination with (NH$_4$)$_2$HPO$_4$ in such an amount that Na was contained therein in such proportions, based on Ca, as shown in FIG. 10.

Preparation of porous sintered sodium hydroxyapatite compacts

Porous sintered sodium hydroxyapatite materials having different Na contents were prepared in the same manner as in Example 2, except that sodium hydroxyapatite powders obtained above were used instead of the hydroxyapatite powder.

Measurement of electrical resistance of carbon dioxide detection element

Carbon dioxide detection elements were prepared by providing electrodes at the both ends of the porous sintered material of the sodium hydroxyapatite obtained above.

For comparison, the electrical resistance (Ro) of the element prepared in Example 3, which did not contain Na, was measured.

Thereafter, the electrical resistance (R) of each element obtained as described above was measured, and the ratio R/Ro was recorded.

Results obtained are shown in FIG. 10. It can be understood that the sodium hydroxyapatite has electrical resistance lower than that of the hydroxyapatite and that the electrical resistance decreases with an increase in Na content.

EXAMPLE 6

Change in electrical resistance of hydroxyapatite due to the change in the concentration of carbon dioxide The porous sintered hydroxyapatite detection element prepared in Example 3 was placed in a tube having an inner diameter of 40 mm, and its electrical resistance (Ro) was measured while blowing air thereinto. Thereafter, a gas containing 1% by volume of carbon dioxide and heated to 1,000° C. was introduced into the tube, the change in its electrical resistance was measured with a lapse of time, and the ratio R/Ro was recorded. Forty minutes after the introduction of the gas, the kind of gas blown into the tube was changed to one containing 10% by volume of carbon dioxide and heated at 1,000° C., the change in the electrical resistance (R) of the element was measured, and the ratio R/Ro was recorded. Forty minutes after the changeover, the kind of gas blown into tube was again changed to one containing 50% by volume of carbon dioxide and heated at 1,000° C. The change in its electrical resistance (R) was measured with a lapse of time, and the ratio R/Ro was recorded. Forty minutes after the changeover, the kind of gas blown into the tube was further changed to a 100% carbon dioxide gas heated at 1,000° C. The change in its electrical resistance (R) was measured with a lapse of time, and the ratio R/Ro was recorded.

Figure 11:
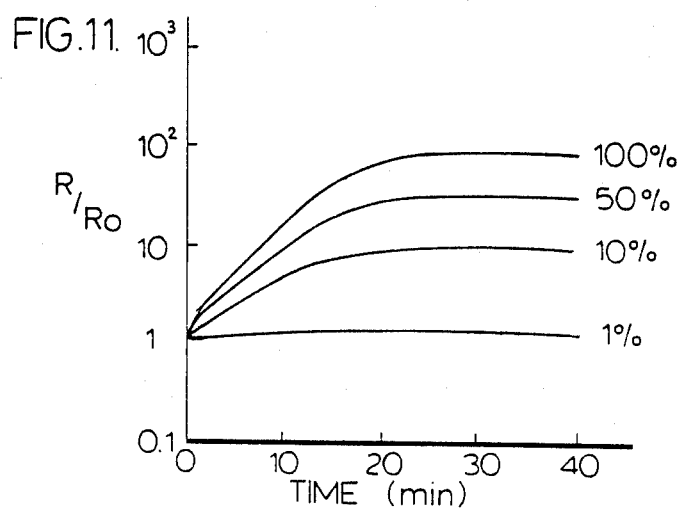
FIG. 11 is a graph showing the change in the electrical resistance of a hydroxyapatite due to the change in the concentration of carbon dioxide gas contacted with it.

Results obtained are shown in FIG. 11. It can be understood from the results that the presence of carbon dioxide can be detected through an increase in electrical resistance of the element when the content of carbon dioxide contained in the gas exceeds 10% by volume although no significant change in electrical resistance was observed even after 40 minutes in the case where the gas contained carbon dioxide of only 1% by volume.

EXAMPLE 7

Preparation of porous sintered hydroxyapatite material and its characteristics as a sensor To 30 g of the hydroxyapatite powders prepared in Example 1 was added 10 ml of an aqueous 5% methyl cellulose solution. The mixture was well kneaded to form a slurry of the hydroxyapatite. The thus prepared slurry was charged into a mold (inner size: 50×20×20 mm). After 6 hours, the bottom of the mold was removed, and the molded article was pushed out of the mold and air dried for 48 hours. The dried molded article was placed in an electric furnace and sintered at a temperature of 1,000° C. for a period of 1 hour. At the both ends of the thus prepared porous sintered material were then formed electrodes by coating with a Pt paste, followed by baking at a temperature of 850° C. for a period of 15 minutes.

Measurement of response characteristics of porous sintered material to the change in concentration of carbon dioxide The electrical resistance (Ro) in air of the porous sintered element obtained above was measured. The element was placed in the center of a tube having an inner diameter of 40 mm, and air heated at a temperature of 900° C. was introduced into the tube and flowed through it. After 10 minutes, a pure carbon dioxide gas heated at 900° C. was introduced into the tube and flowed through it. The change in the electrical resistance (R) of the porous sintered element was measured, and the ratio R/Ro was recorded. Forty minutes after the introduction of the carbon dioxide gas, the kind of gas flowed through the tube was changed to air heated at 900° C. The change in the electrical resistance (R) of the element was measured, and the ratio R/ROD was recorded. Forty minutes after the introduction of air, i.e., 80 minutes after the introduction of the carbon dioxide gas, the kind of gas flowed through the tube was again changed to a carbon dioxide gas heated at 900° C. The change in electrical resistance (R) of the element was measured, and the ratio R/Ro was recorded.

Figure 12:
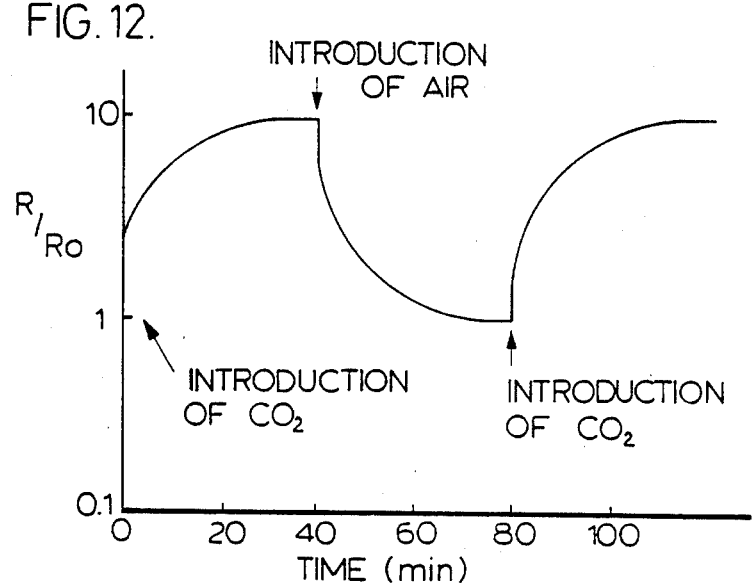
FIG. 12 is a graph showing the sensing characteristics of a carbon dioxide detection element made of a porous sintered material of a hydroxyapatite according to the invention.

Results obtained are shown in FIG. 12. In this figure, the abscissa indicates the time elapsed after the first introduction of the carbon dioxide gas.

FIG. 12 shows that the electrical resistance of the element increases quickly after the introduction of carbon dioxide gas and decreases quickly after the introduction of air. It can therefore be understood that the element made of a porous sintered material exhibits sharp response characteristics to carbon dioxide gas.

EXAMPLE 8

Preparation of thin layer type detection element of hydroxyapatite and its characteristics as a sensor The thin layer porous sintered hydroxyapatite element (which was formed on an alumina plate) prepared in Example 3 was placed in a tube having an inner diameter of 40 mm, and its electrical resistance (Ro) was measured while air was flowed through the tube. After air heated at 900° C. was flowed through the tube for 10 minutes, the gas being flowed through it was changed to a pure carbon dioxide gas heated at 900° C. The change in electrical resistance (R) of the element was measured with a lapse of time, and the ratio R/Ro was recorded. Forty minutes after the introduction of the carbon dioxide gas, the gas being flowed through the tube was changed to air heated at 900° C. The change in electrical resistance (R) of the element was measured, and the ratio R/Ro was recorded. Forty minutes after the introduction of the air, i.e., 80 minutes after the first introduction of the carbon dioxide gas, the gas being flowed through the tube was again changed to a carbon dioxide gas heated at 900° C. The change in electrical resistance (R) of the element was measured with a lapse of time, and the ratio R/Ro was recorded.

Figure 13:
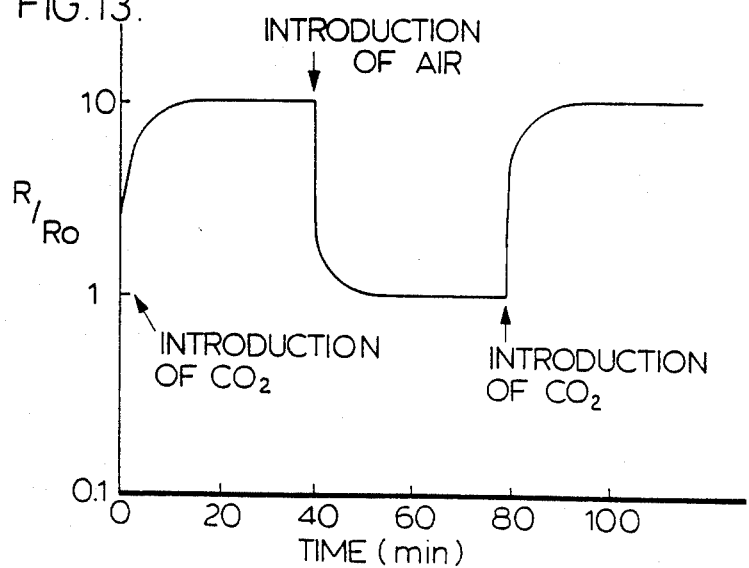
FIG. 13 is a graph showing the sensing characteristics of a carbon dioxide gas detection element made of a thin layer of a hydroxyapatite according to the invention.

Results obtained are shown in FIG. 13. It can be understood that a thin layer hydroxyapatite element formed on an alumina plate also exhibits sharp response characteristics to carbon dioxide gas, as in the case of Example 7.

EXAMPLE 9

(1) Preparation of Sample (1-1) Reference sample

One gram of powders of a high purity hydroxyapatite (AN 830425, manufactured by Central Glass Co., Ltd.) was charged into a pellet molding machine and pressed at a pressure of 200 kg/cm$^2$ to form a pellet having a diameter of 20 mm. The pellet was heated in air at a temperature of 900° C. for a period of 2 hours by means of an electric furnace to give a sintered material.

The thus obtained sintered material was cut into sections with a size of 15 mm (in length) by 10 mm (in width) and then polished. A ruthenium oxide paste was coated on the cut piece to form an electrode, and a platinum wire lead was bonded thereto. The paste was allowed to dry in a drier at a temperature of from 90° to 100° C. Thereafter, the wired piece was baked in air at a temperature of 850° C. for a period of 15 minutes to give a carbon dioxide gas detection element provided with electrodes as shown in FIG. 5.

(1-2) Sample incorporated with sodium carbonate

Into 100 ml of distilled water maintained at 20° C. was dissolved 3.50 g of sodium carbonate ($Na_2CO_3$). In the resulting aqueous sodium carbonate solution was immersed the detection element prepared in (1-1) above, the immersing treatment being effected in two stages: at a reduced pressure of 1/10 atm. for a period of 30 minutes and then at atmospheric pressure for 16 hours. The resulting element was placed in a drier, and dried at a temperature of from 90° to 100° C. for a period of 2 hours to give a carbon dioxide gas detection element incorporated with sodium carbonate.

Aqueous sodium carbonate solutions having different sodium carbonate concentrations were prepared. Carbon dioxide detection elements prepared as in (1-1) above were immersed in one of the sodium carbonate solutions and treated in the same manner as above to give carbon dioxide gas detection elements incorporated with different amounts of sodium carbonate.

(1-3) Sample incorporated with sodium carbonate

Into 20 ml of 3N HCl maintained at 20° C. was dissolved 3.31 g of calcium carbonate ($CaCO_3$). The pH of the resulting solution was adjusted to from 9 to 10 by the addition of 2N ammonia water. Thereafter, distilled water was added thereto to make its total volume 100 ml.

In the resulting aqueous calcium carbonate solution was immersed a detection element prepared as in (1-1) above and then treated in the same manner as in (1-2)

above to give a carbon dioxide gas detection element incorporated with calcium carbonate.

Aqueous calcium carbonate solutions containing different amounts of calcium carbonate were prepared in the same manner as above. The carbon dioxide detection element prepared in (1-1) above was immersed in each of the calcium carbonate solutions and treated in the same manner as above to give a carbon dioxide gas detection element incorporated with a different amount of calcium carbonate.

(2) Test Method

(2-1) Measurement of electrical resistance (i) Reference sample

The reference sample prepared in (1-1) above was placed in an electric furnace maintained at 600° C., and its electrical resistance (Ro) in air was measured.

(ii) Sample incorporated with sodium carbonate

The sample incorporated with sodium carbonate prepared in (1-2) above was placed in the electric furnace, in place of the reference sample, and its electrical resistance (R) was measured under the same conditions as in (i) above. The ratio of the electrical resistance (R/Ro) was calculated.

The above measurement was repeated, using the samples incorporated with different amounts of sodium carbonate prepared in (1-2) above, and the ratio R/Ro was calculated for each sample.

(iii) Sample incorporated with calcium carbonate

The ratio R/Ro was measured for each of the samples incorporated with calcium carbonate prepared in (1-3) above, in the same manner as in (ii) above.

(2-2) Determination of sensitivity to carbon dioxide gas (i) Reference Sample A reference sample was placed in an electric furnace maintained at 500° C., and its electrical resistance (Ro) in air was measured. Thereafter, the air in the electric furnace was replaced with a pure carbon dioxide gas heated to the same temperature. The change in the electrical resistance of the sample was measured for the period of time shown in FIGS. 14 and 15, and the ratio R/Ro was calculated.

The above measurement was repeated, except that the temperature of the electric furnace was maintained at 600° C., and the ratio R/Ro at 600° C. was also calculated.

(ii) Sample incorporated with sodium carbonate

The above measurement conducted at 500° C. and 600° C. was repeated in the same manner as above, using the sample subjected to the immersing treatment in a solution of 3.50 g of sodium carbonate in 100 g of water, instead of the reference sample, and the ratio R/Ro was calculated.

(iii) Sample incorporated with calcium carbonate

The above measurement conducted at 500° C. and 600° C. was repeated in the same manner as above, using the sample subjected to the immersing treatment in the solution of 3.31 g of calcium carbonate in 100 ml of water, instead of the reference sample, and the ratio R/Ro was calculated.

(3) Test Results

(3-1) Electrical resistance

Sample incorporated with sodium carbonate:
Results obtained are shown in FIG. 14.

Figure 14:
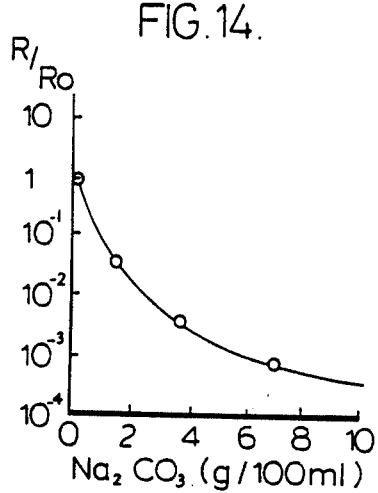
FIG. 14 is a graph showing the relationship between the content of sodium carbonate in a hydroxyapatite-sodium carbonate composite according to the invention, used in Example 9, and its electrical resistance.

In FIG. 14, the ordinate indicates the ratio (R/Ro) of the electrical resistance (R) of the sample incorporated with sodium carbonate to that (Ro) of the reference sample; and the abscissa indicates the amount of sodium carbonate used in the immersing treatment in the preparation (indicated as grams of sodium carbonate contained in 100 ml of water used for the treatment).

Sample incorporated with calcium carbonate:
Results obtained are shown in FIG. 15.

Figure 15:
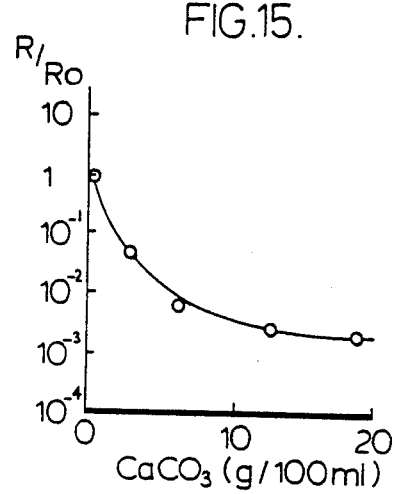
FIG. 15 is a graph showing the relationship between the content of calcium carbonate in a hydroxyapatite-calcium carbonate composite according to the invention, used in Example 9, and its electrical resistance.

In FIG. 15, the ordinate indicates the ratio (R/Ro) of the electrical resistance (R) of the sample incorporated with calcium carbonate to that (Ro) of the reference sample; and the abscissa indicates the amount of calcium carbonate used in the immersing treatment in the preparation (indicated as grams of calcium carbonate used therefor).

It can be understood from FIGS. 14 and 15 that the electrical resistance of the samples measured at 600° C. is markedly reduced due to the incorporation of sodium carbonate or calcium carbonate into the hydroxyapatite. It can be seen through the comparison of the results shown in FIGS. 14 and 15 that the reduction in electrical resistance of the samples incorporated with sodium carbonate is slightly superior to that of the samples incorporated with calcium carbonate.

(3-2) Sensitivity to carbon dioxide gas

Figure 16:
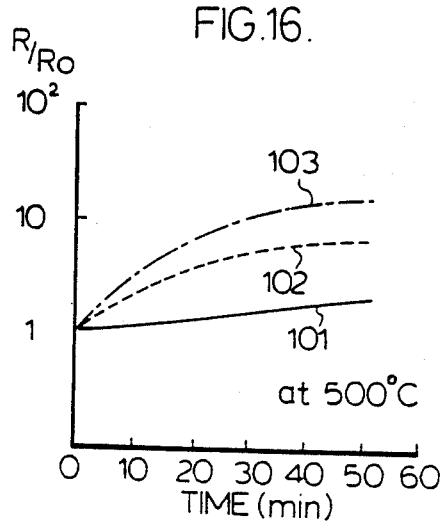
FIG. 16 is a graph showing sensitivities for detecting carbon dioxide gas of a hydroxyapatite, a hydroxyapatite-sodium carbonate composite and a hydroxyapatite-calcium carbonate composite at a temperature of 500° C., as tested in Example 9.
Figure 17:
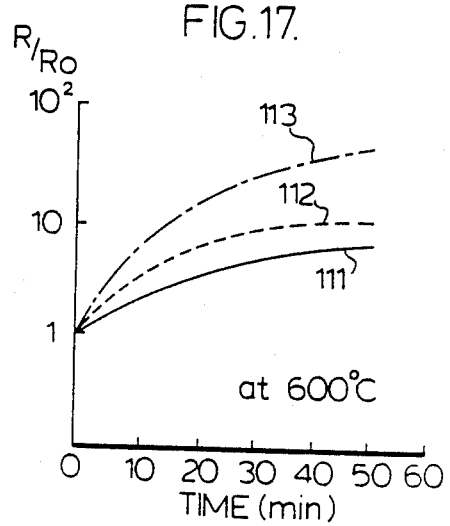
FIG. 17 is a graph showing the sensitivities of the same materials as in FIG. 16 at a temperature of 600° C., as tested in Example 9.

Results obtained in the measurement at 500° C. are shown in FIG. 16, and the results obtained in the measurement at 600° C. are shown in FIG. 17.

In FIGS. 16 and 17, the ordinate indicates the ratio (R/Ro) of the electrical resistance (R) in carbon dioxide gas to that (Ro) in air; and the abscissa indicates the time (in minutes) elapsed between the measurement and the time when the air in the furnace was replaced with a pure carbon dioxide gas. In FIGS. 16 and 17, the continuous curves 101 and 111 show the results with the reference sample; the dotted curves 102 and 112 show the results with the sample incorporated with sodium carbonate; and the chained curves 103 and 113 show the results with the sample incorporated with calcium carbonate.

It can be understood from FIGS. 16 and 17 that the increase in electrical resistance due to the presence of carbon dioxide gas in contact with the detection element becomes more significant as a result of the incorporation of sodium carbonate or calcium carbonate and, therefore, carbon dioxide contained in a gas can be detected with an increased sensitivity. The improvement in sensitivity to carbon dioxide in a gas in the sample incorporating with calcium carbonate is more significant than that in the sample incorporated with sodium carbonate. It can be seen by comparing the results in FIGS. 16 and 17 that the sensitivity for detecting carbon dioxide gas at 600° C. is higher than that at 500° C. However, in the comparison with the reference sample, the improvement in the sensitivity at 500° C. is greater than that at 600° C. The presence of carbon dioxide gas can, therefore, be readily detected at a temperature not higher than 500° C., e.g., at a temperature of from 300° to 500° C.

EXAMPLE 10

The effect of the incorporation of calcium chloride into the hydroxyapatite on the sensitivity for detecting carbon dioxide gas.

(1) Preparation of Sample

(1-1) Reference sample

Figure 18:
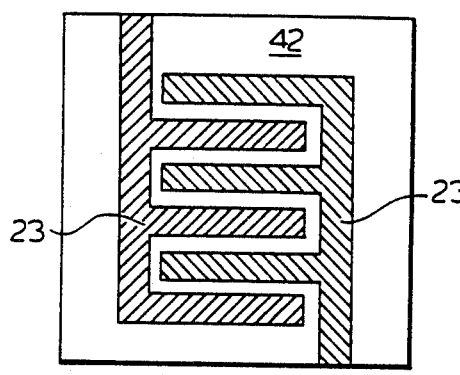
FIG. 18 is a planar view showing an alumina substrate or base used in Example 10, which shows an example of the arrangement of electrodes in a carbon dioxide gas detection element according to the invention.

Into 45 ml of ethanol was dissolved 20 g of butylcarbinol. Twenty grams of powdered, high purity hydroxyapatite (AN 830425, manufactured by Central Glass Co., Ltd.) was added to the solution and well admixed to form a uniform dispersion. The thus prepared dispersion was shaped into a sheet having a thickness of 200 μm by a doctor blade method. The resulting sheet was then cut into a piece of 1 cm × 1 cm. The piece was placed on electrodes on an alumina plate prepared by forming combshaped electrodes 23 and 23, as shown in FIG. 18, of ruthenium oxide on an alumina substrate or base 42 with a size of 2.5 cm 2.5 cm by means of a screen printing. After drying at room temperature, it was placed in an electric furnace filled with air. The temperature in the furnace was raised to 500° C. and maintained at the same temperature for a period of 2 hours, and then it was raised to 800° C. and maintained at the same temperature for a period of 2 hours. To the electrodes of the thus prepared sintered thin plate sample were bonded wire leads to give a carbon dioxide gas detection element.

(1-2) Sample incorporated with calcium chloride

Into 50 ml of distilled water was dissolved 1.84 g (0.02 mole) of calcium chloride, and the pH of the resulting solution was adjusted to between 9 and 10 by adding aqueous ammonia. Thereafter, distilled water was added to the solution to make its total volume 100 ml. The carbon detection element prepared as in (1-1) above was immersed in the resulting calcium chloride solution (concentration of calcium chloride: 0.2 mol/l) under a reduced pressure of 1/10 atm. for a period of 30 minutes and then at atmospheric pressure for a period of 16 hours. It was dried in a drier at a temperature of from 90° C. to 100° C., and then provided with wire leads at the electrodes thereof to give a carbon dioxide gas detection element (Ca-1).

A carbon dioxide gas detection element (Ca-2) was prepared in the same manner as above, except that a solution containing 0.02 mol/l of calcium chloride was used instead of the solution containing 0.2 mol/l of calcium chloride.

A carbon dioxide gas detection element (Ca-3) was prepared in the same manner as above, except that a solution containing 0.002 mol/l of calcium chloride was used instead of the solution containing 0.2 mol/l of calcium chloride.

(2) Test Method

(2-1) Measurement of sensitivity of reference sample

The reference carbon dioxide detection element prepared in (1-1) above was placed in an electric furnace maintained at 400° C. by a temperature controller and filled with air, and the electrical resistance (Ro) of the reference element in air was measured. Thereafter, the air in the electric furnace was replaced with air containing 0.1%, 1.0% or 10% of carbon dioxide, and the electrical resistance (R) of the reference element was measured in each of the gases. The ratio R/Ro, i.e., [electrical resistance of the reference element measured in air containing carbon dioxide gas]/[electrical resistance of the reference element measured in air], was calculated for each case.

(2-2) Sensitivity of element incorporated with calcium chloride

The carbon dioxide detection element (Ca-1) was placed in an electric furnace maintained at 400° C. by a temperature controller and filled with air, and the electrical resistance (Ro) of the element in air was measured. Thereafter, the air in the electric furnace was replaced with air containing 1% of carbon dioxide, the electrical resistance (R) of the element was measured, and the ratio R/Ro was calculated therefrom.

The carbon dioxide gas detection elements (Ca-2) and (Ca-3) were subjected to the same measurement as above to measure their electrical resistances Ro and R, and the ratio R/Ro was calculated therefrom.

(3) Test Results

(3-1) Reference sample

Figure 19:
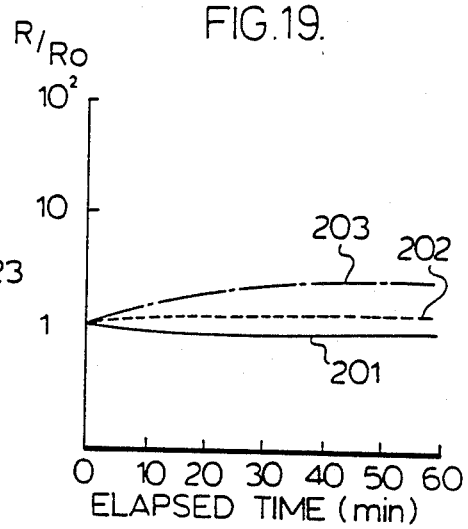
FIG. 19 is a graph showing the test results in Example 10 obtained with a reference element for detecting carbon dioxide gas.

Results as shown in FIG. 19 were obtained.

In FIG. 19, the ordinate indicates the ratio R/Ro, i.e., [electrical resistance of the reference sample measured in air containing carbon dioxide gas]/[electrical resistance of the reference sample measured in air]; and the abscissa indicates the period of time elapsed after the replacement of the air in the electric furnace with air containing carbon dioxide.

In FIG. 19, the continuous curve 201 shows the results obtained in the air containing 0.1% of carbon dioxide; the dotted curve 202 the results in the air containing 1% of carbon dioxide; and the chained curve 203 the results in the air containing 10% of carbon dioxide.

(3-2) Sample incorporated with calcium chloride

Figure 20:
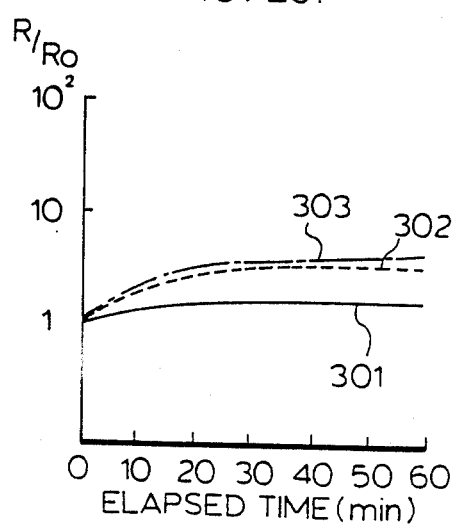
FIG. 20 is a graph showing the test results in Example 10 obtained with a carbon dioxide gas detection element according to the invention incorporated with calcium chloride.

Results as shown in FIG. 20 were obtained.

In FIG. 20, the ordinate indicates the ratio R/Ro, i.e., [electrical resistance of the sample incorporated with calcium chloride measured in air containing carbon dioxide]/[electrical resistance of the sample incorporated with calcium chloride measured in air]; and the abscissa indicates the period of time elapsed after the replacement of the air in the electric furnace with air containing carbon dioxide.

In FIG. 20, the continuous curve 301 shows the results obtained by the carbon dioxide detection element (Ca-3); the dotted curve 302 the results by the carbon dioxide detection element (Ca-2); and the chained curve 303 the results by the carbon dioxide detection element (Ca-1).

EXAMPLE 11

The effect of the incorporation of calcium chloride and platinum into the hydroxyapatite on the sensitivity for detecting carbon dioxide gas.

(1) Preparation of samples

Ruthenium oxide electrodes were formed by means of a screen printing on the same alumina substrate as in Example 10 having a size of 2.5 cm × 2.5 cm, and a platinum paste was coated on the electrodes. A piece of the hydroxyapatite sheet prepared in (1-1) in Example 10 was placed on the electrodes and treated in the same manner as in (1-1) in Example 10 to give a thin plate sample. Wire leads were attached to the electrodes of the thin plate sample to give a carbon dioxide gas detection element incorporated with platinum.

The thus prepared element was immersed in a solution containing 0.2 mol/l of calcium chloride in the same manner as in (1-2) in Example 10 to give a carbon dioxide gas detection element (Ca-Pt-1).

Carbon dioxide gas detection elements (Ca-Pt-2) and (Ca-Pt-3) were prepared in the same manner as above, except that a solutions containing 0.02 mol/l and 0.002 mol/l of calcium chloride was used, respectively, instead of the solution containing 0.2 mol/l of calcium chloride.

(2) Test Method

The electrical resistances Ro and R of the carbon dioxide gas detection elements (Ca-Pt-1), (Ca-Pt-2) and (Ca-Pt-3) were measured in the same manner as in (2-2) in Example 10, and the ratio R/Ro of the electrical resistance was calculated therefrom.

(3) Test Results

Figure 21:
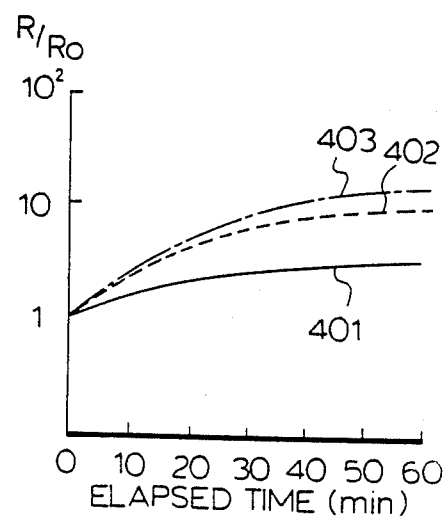
FIG. 21 is a graph showing the results of the test in Example 11.

Results as shown in FIG. 21 were obtained.

In FIG. 21, the ordinate indicates the ratio R/Ro, i.e., [electrical resistance of the sample incorporated with calcium chloride and platinum measured in the air containing carbon dioxide gas]/[electrical resistance of the sample incorporated with calcium chloride and platinum measured in air]; and the abscissa indicates the period of time elapsed after the replacement of the air in the electric furnace with the air containing 1.0% of carbon dioxide.

In FIG. 21, the continuous curve 401 shows the results obtained by the carbon dioxide gas detection element (Ca-Pt-3); the dotted curve 402 the results by the element (Ca-Pt-2); and the chained curve 403 the results by the element (Ca-Pt-1).

EXAMPLE 12

The effect of the incorporation of calcium chloride, palladium chloride and platinum into the hydroxyapatite on the sensitivity for detecting carbon dioxide gas.

(1) Preparation of Sample

Into 50 ml of distilled water were dissolved 1.84 g (0.02 mol) of calcium chloride and 0.1 g ($5 \times 10^{-4}$ mol) of palladium chloride, and the pH of the resulting solution was adjusted to 9 to 10 by adding aqueous ammonia. Thereafter, distilled water was added to the solution to make its total volume 100 ml. The carbon dioxide gas detection element prepared in (1) in Example 11 was immersed in the resulting solution (concentration of calcium chloride: 0.2 mol/l; and concentration of palladium chloride: $5 \times 10^{-3}$ mol/l) under a reduced pressure of 1/10 atm. for a period of 30 minutes and then at atmospheric pressure for a period of 16 hours. It was dried in a drier at a temperature of from 90° C. to 100° C., and then provided with wire leads at the electrodes to give a carbon dioxide gas detection element (Ca-Pd-Pt-1).

A carbon dioxide gas detection element (Ca-Pd-Pt-2) was prepared in the same manner as above, except that a solution containing 0.2 mol/l of calcium chloride and $5 \times 10^{-4}$ mol/l of palladium chloride was used instead of the solution containing 0.2 mol/l of calcium chloride and $5 \times 10^{-3}$ mol/l of palladium chloride.

A carbon dioxide gas detection element (Ca-Pd-Pt-3) was prepared in the same manner as above, except that a solution containing 0.2 mol/l of calcium chloride and $5 \times 10^{-5}$ mol/l of palladium chloride was used instead of the solution containing 0.2 mol/l of calcium chloride and $5 \times 10^{-3}$ mol/l of palladium chloride.

(2) Test Method

The electrical resistances Ro and R of the carbon dioxide gas detection elements (Ca-Pd-Pt-1), (Ca-Pd-Pt-2) and (Ca-Pd-Pt-2) were measured in the same manner as in 2-2) in Example 10, and the ratio R/Ro of the electrical resistance was calculated therefrom.

(3) Test Results

Results as shown in FIG. 22 were obtained.

In FIG. 22, the ordinate indicates the ratio R/Ro, i.e., [electrical resistance of the sample incorporated with calcium chloride, palladium chloride and platinum measured in air containing carbon dioxide gas]/[electrical resistance of the sample incorporated with calcium chloride, palladium chloride and platinum in air]; and the abscissa indicates the period of time elapsed after the replacement of the air in the electric furnace with the air containing carbon dioxide.

In FIG. 22, the continuous curve 501 shows the results obtained by the carbon dioxide gas detection element (Ca-Pd-Pt-3); the dotted curve 502 the results by the element (Ca-Pd-Pt-2); and the chained curve 503 by the element (Ca-Pd-Pt-1).

EXAMPLE 13

The effect of a heating-and-cooling treatment on the sensitivity of an element incorporated with calcium chloride, palladium chloride and platinum.

(1) Preparation of Sample

A carbon dioxide gas detection element (Ca-Pd-Pt-1) was prepared in the same manner as in (1) in Example 12, using a solution containing 0.2 mol/l of calcium chloride and $5 \times 10^{-3}$ mol/l of palladium chloride.

(2) Test Method

The carbon dioxide gas detection element (Ca-Pd-Pt-1) was placed in an electric furnace maintained at 400° C. by means of a temperature controller, and the electrical resistance (Ro) of the element in air was measured. Thereafter, the air in the electric furnace was replaced with air containing 0.1% of carbon dioxide, and the change in the electrical resistance ($R_1$) of the element was measured with a lapse of time.

The carbon dioxide gas detection element (Ca-Pd-Pt-1) was placed in an electric furnace maintained at 400° C. by means of a temperature controller, and the electrical resistance (Ro) of the element in air was measured. The element was taken out of the furnace and allowed to cool to room temperature. The element was again placed in the electric furnace, and the air in the furnace was replaced with air containing 0.1% of carbon dioxide. The change in the electrical resistance ($R_2$) of the element was measured with a lapse of time.

(3) Test Results

Results as shown in FIG. 23 were obtained.

In FIG. 23, the ordinate indicates the ratio R1/Ro or R2/Ro, i.e., [electrical resistance of the element measured in air containing carbon dioxide]/[electrical resistance of the element measured in air]; and the abscissa indicates the period of time elapsed after the replacement of the air in the electric furnace with the air containing carbon dioxide gas.

In FIG. 23, the continuous curve 601 shows the results obtained with respect to the detection element in which the heating-and-cooling treatment was not carried out; and the dotted curve 602 shows the results obtained with respect to the detection element in which the heating-and-cooling treatment was carried out.

EXAMPLE 14

The effect of carbon dioxide gas conditioning on a carbon dioxide gas detection element incorporated with calcium chloride, palladium chloride and platinum.

(1) Preparation of Sample

A carbon dioxide gas detection element (Cd-Pd-Pt-1) was prepared in the same manner as in (1) in Example 12, using a solution containing 0.2 mol/l of calcium chloride and $5 \times 10^{-3}$ mol/l of palladium chloride.

(2) Test Method

The carbon dioxide gas detection element (Ca-Pd-Pt-1) was placed in an electric furnace maintained at 400° C. by means of a temperature controller, and the electrical resistance (Ro) of the element in air was measured. Thereafter, the air in the electric furnace was replaced with an air containing 0.1% of carbon dioxide, and the change in the electrical resistance ($R_3$) of the element was measured with a lapse of time. The element was taken out of the furnace and allowed to cool to room temperature. The element was again placed in the electric furnace, and the air in the furnace was replaced with air containing 0.1% of carbon dioxide. The change in the electrical resistance ($R_4$) of the element was measured with a lapse of time.

(3) Test Results

Results as shown in FIG. 24 were obtained.

In FIG. 24, the ordinate indicates the ratio $R_3$/Ro or $R_4$/Ro, i.e., [electrical resistance of the element measured in air containing carbon dioxide gas]/[electrical resistance of the element measured in air]; and the abscissa indicates the period of time elapsed after the replacement of the air in the electric furnace with the air containing carbon dioxide gas.

In FIG. 24, the continuous curve 701 shows the results obtained with respect to the detection element in which the treatment with carbon dioxide gas was not carried out; and the dotted curve 702 shows the results obtained with respect to the detection element in which the treatment with carbon dioxide gas was carried out.

It can be understood by comparing the results shown in FIGS. 20 to 22 that the sensitivity of carbon dioxide gas detection elements utilizing a hydroxyapatite can be improved by the incorporation of calcium chloride, and the improvement in sensitivity becomes remarkably when calcium chloride and platinum are incorporated thereinto. It can also be understood that the improvement becomes more significant when calcium chloride, palladium chloride and platinum are incorporated thereinto.

It can further be understood by comparing the results shown in FIGS. 23 and 24 that the sensitivity of a carbon dioxide gas detection element can be improved further when it is given a heat history, or subjected to a heating-and-cooling treatment, and that the improvement becomes more significant when it is given a heat history, wherein it is heated in a gas containing carbon dioxide and then cooled.

While a preferred embodiment of the invention has been shown and described in detail, it will be apparent that various modifications and alternations may be made thereto without departing the scope and spirit of the invention.

What we claim is:

1. A method for the detection of carbon dioxide gas comprising bringing carbon dioxide containing gas into contact with a detection element comprising a hydroxyapatite according to the formula (I):

$$M_{10}(ZO_4)_6(OH)_2 \qquad (I)$$

wherein M is an element selected from the group consisting of Ca, Ba, Sr, Pb and Cd, and Z is an element selected from the group consisting of P, As, and V; and measuring the change in the electrical resistance of said detection element.

2. A method according to claim 1 further comprising drying said carbon dioxide containing gas by passing the gas through a means for dehumidification before bringing said gas into contact with said detection element.

3. A method according to claim 1 further comprising heating said carbon dioxide containing gas before bringing said gas into contact with said detection element.

4. A method according to claim 1 further comprising heating said detection element.

* * * * *